United States Patent
Katsuyama (10) Patent No.: US 8,708,910 B2
(45) Date of Patent: *Apr. 29, 2014

(54) ULTRASONIC DIAGNOSIS APPARATUS AND ULTRASONIC DIAGNOSIS METHOD

(75) Inventor: Kimito Katsuyama, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 100 days.

This patent is subject to a terminal disclaimer.

(21) Appl. No.: 13/067,807

(22) Filed: Jun. 28, 2011

(65) Prior Publication Data

US 2012/0004550 A1 Jan. 5, 2012

(30) Foreign Application Priority Data

Jun. 30, 2010 (JP) .................................. 2010-149208

(51) Int. Cl.
*A61B 8/00* (2006.01)

(52) U.S. Cl.
USPC ............ 600/437; 600/407; 600/443; 600/447

(58) Field of Classification Search
USPC .................................. 600/407, 437, 443, 447
See application file for complete search history.

(56) References Cited

U.S. PATENT DOCUMENTS

| | | |
|---|---|---|
| 2003/0092990 A1 | 5/2003 | Baba et al. |
| 2006/0235302 A1 | 10/2006 | Grossman et al. |
| 2009/0003128 A1 | 1/2009 | Jeong et al. |
| 2009/0093721 A1 | 4/2009 | Katsuyama |
| 2010/0076312 A1 | 3/2010 | Katsuyama |

FOREIGN PATENT DOCUMENTS

| | | |
|---|---|---|
| EP | 0256686 A1 | 2/1988 |
| EP | 1262148 A1 | 12/2002 |
| JP | 05-95946 | 4/1993 |
| JP | 06-105841 | 4/1994 |
| JP | 63-082633 A | 4/1998 |
| JP | 2001-252276 A | 9/2001 |
| JP | 2003-070788 A | 3/2003 |
| JP | 2007-007045 | 1/2007 |
| JP | 2009-101145 A | 5/2009 |
| JP | 2009-521980 A | 6/2009 |
| JP | 2010-012157 A | 1/2010 |

(Continued)

OTHER PUBLICATIONS

Krucker, et al.; Sound Speed Estimation Using Automatic Ultrasound Image Registration; IEEE Transactions on Ultrasonics, Ferroelectrics and Frequency Control; Sep. 2004; vol. 51, No. 9; The Institute of Electrical and Electronics Engineers, Inc.

(Continued)

*Primary Examiner* — Joel Lamprecht
(74) *Attorney, Agent, or Firm* — Jean C. Edwards, Esq.; Edwards Neils PLLC (57) ABSTRACT

An ultrasonic diagnosis apparatus comprising: an ultrasonic probe which includes a plurality of ultrasonic transducers which transmit ultrasonic waves to an object, receive the ultrasonic waves reflected by the object, and output ultrasonic detection signals; a reception time calculating device which calculates at least one of a reception time and a reception wave at each of elements corresponding to lattice points set in a shallower region than a region of interest in the object; an image generating device which generates an image at a lattice point in the region of interest, based on a hypothetical sound velocity set in the region of interest and the calculated one of the reception time and the reception wave; an image analyzing device which analyzes the generated image; and a local sound velocity calculating device which calculates a local sound velocity in the region of interest, based on a result of the image analysis.

31 Claims, 7 Drawing Sheets

(56) References Cited

FOREIGN PATENT DOCUMENTS

| JP | 2010-99452 | 5/2010 |
|----|------------|--------|
| WO | WO 93/17622 | 9/1993 |
| WO | WO 2007/075040 A1 | 7/2007 |

OTHER PUBLICATIONS

Linzer, et. al.; Ultrasonic Tissue Characterization; Annual Review of Biophysics and Bioengineering; Jun. 1982; pp. 303-329; vol. 11.

Anderson, et. al.; The Direct Estimation of Sound Speed using Pulse-Echo Ultrasound; Journal of the Acoustical Society of America, AIP; Nov. 1998; vol. 104, No. 5; Melville, New York.

Schomberg; An Improved Approach to Reconstructive Ultrasound Tomography; Journal of Physics D: Applied Physics; 1978; pp. L181-L185; vol. 11, No. 15.

Notification of Reasons for Rejection issued by the Japanese Patent Office (JPO) on Sep. 27, 2013, in connection with Japanese patent application No. 2010-149208.

ULTRASONIC DIAGNOSIS APPARATUS AND ULTRASONIC DIAGNOSIS METHOD

CROSS-REFERENCE TO RELATED APPLICATIONS

The present invention claims priority from Japanese Patent Application No. 2010-149208, filed on Jun. 30, 2010, the contents of which are herein incorporated by reference in their entirety.

BACKGROUND OF THE INVENTION

1. Field of the Invention

The present invention generally relates to an ultrasonic diagnosis apparatus and an ultrasonic diagnosis method, and more particularly, to an ultrasonic diagnosis apparatus and an ultrasonic diagnosis method which are used to capture and display ultrasonic images of an object with the use of ultrasonic waves, and are used in diagnosing tissues.

2. Description of the Related Art

Conventionally, a sound velocity value in a portion (a diagnosed site) in an object (such a sound velocity value will be hereinafter referred to as a local sound velocity value) is measured with the use of ultrasonic waves. For example, the following methods have been suggested. According to one of the methods, two oscillators for transmission and reception are positioned to face each other, and a sound velocity value in an object is calculated from the distance between the oscillators and the period for propagation of ultrasonic waves between the oscillators. According to another one of the methods, two sets of oscillators arranged at predetermined intervals are used for transmission and reception, and a propagation velocity is calculated from the period for ultrasonic propagation between the oscillators, transmission and reception angles, and the distances between the oscillators in the respective pairs.

Japanese Patent Application Laid-Open No. 5-95946 discloses the following method of measuring values of local sound velocities. According to Japanese Patent Application Laid-Open No. 5-95946, ultrasonic waves are transmitted while the output angle from a transmission oscillator toward an object is being varied, and ultrasonic waves are received while the incident angle is being varied by a reception oscillator. All the periods of time elapsed from transmission to reception are stored into a memory. A hypothetical distribution of sound velocities is set, and, based on the distribution of sound velocities, the elapsed time is calculated for each of the output angles and incident angles. The hypothetical distribution of sound velocities is then corrected so that the differences between the calculated values of period of elapsed time and actual measurement values are minimized. The sound velocity value in the object is then determined from the resultant distribution of sound velocities.

Figure 7A:
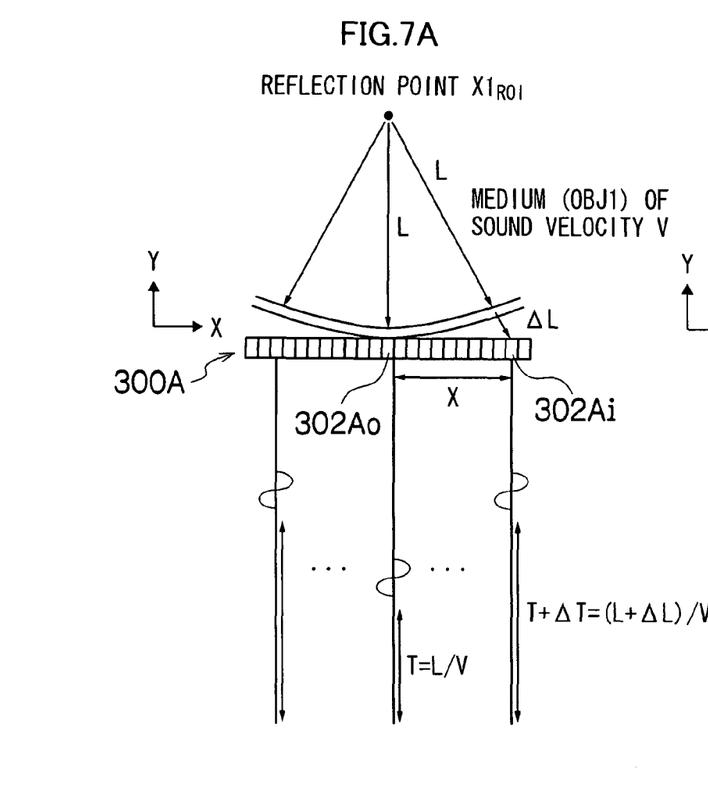
FIG. 7 is an explanatory view schematically showing an operation to calculate the value of a local sound velocity.

A sound velocity value V in an object OBJ1 made of a medium having a constant sound velocity value can be calculated in the following manner. As shown in FIG. 7A, where L represents the distance from a reflection point (region) $X1_{ROI}$ in the object OBJ1 to an ultrasonic probe 300A, the period of time T elapsed from reflection of ultrasonic waves at the reflection point $X1_{ROI}$ to reception of the ultrasonic waves by an element $302A_0$ located immediately below the reflection point $X1_{ROI}$ is expressed as T=L/V. Where the period of time elapsed before reception by an element $302A_1$ located at a distance X in the X-direction (the array direction of elements 302A) from the element $302A_0$ is expressed as T+ΔT, the delay time ΔT between the elements $302A_0$ and $302A_1$ is expressed by the following mathematical formula (1):

$$\Delta T = \Delta L/V \text{ (where } \Delta L = \sqrt{(L^2+X^2)}-L) \tag{1}$$

Therefore, after the ultrasonic waves are reflected at the reflection point $X1_{ROI}$ the time T after the transmission of the ultrasonic waves, the periods of time 2T and 2T+ΔT elapsed before the ultrasonic waves are received by the element $302A_0$ and another element are measured. In this manner, the distance L to the reflection point $X1_{ROI}$ and the velocity V can be uniquely determined.

Where the ultrasonic waves reflected from the reflection point $X1_{ROI}$ can be clearly recognized, the distance L and the velocity V can be determined from the elapsed time measured at the element $302A_0$ and another element. However, ultrasonic detection signals which are output from the respective elements 302A are normally resulted from interferences by signals from numerous reflection points, and it is difficult to distinguish only the signals supplied from a specific reflection point. Therefore, in practice, the distance L to the reflection point $X1_{ROI}$, the delay time ΔT, and the sound velocity value V are uniquely determined from the spatial frequency, sharpness, and contrast in a re-formed image in a region of interest in the vicinity of the reflection point $X1_{ROI}$.

Figure 7B:
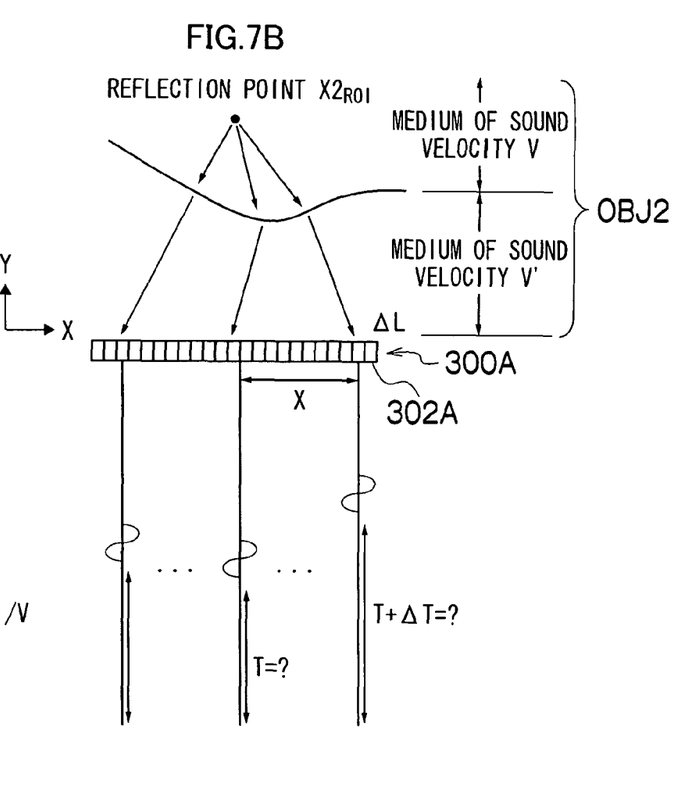

As described above, where the sound velocity in an object is uniform, the value of the sound velocity can be calculated. When the internal sound velocity is not uniform as in an object OBJ2 shown in FIG. 7B, however, it is difficult to calculate the distance L to a reflection point (region) $X2_{ROI}$ and the sound velocity values V and V' by the above described method.

To counter this problem, the applicant suggested a method of determining a local sound velocity where the sound velocity in an object is not uniform (Japanese Patent Application Laid-Open No. 2010-99452). According to this method, a hypothetical sound velocity is set in a region of interest in an object, and an optimum sound velocity value at a lattice point set in a shallower region than the region of interest is set. Based on the hypothetical sound velocity and the optimum sound velocity value, an image of the region of interest is generated from reception signals of the respective elements obtained when ultrasonic waves are transmitted to the region of interest, and the image of the region of interest is then analyzed. Alternatively, an optimum sound velocity value or a reception wave at a representative lattice point in the region of interest is calculated. The local sound velocity value in the region of interest is then determined by comparing the hypothetical sound velocity in the region of interest with the optimum sound velocity value or the reception wave calculated based on the optimum sound velocity value set in the shallower region than the region of interest. As described above, the method suggested previously by the present applicant is a method of approximating the reception wave at each lattice point by the ambient sound velocity (an optimum sound velocity), and this method enables measurements of local sound velocities even where the sound velocity in the object is not uniform.

Where the unsteadiness of the sound velocity in the object is higher than predicted, however, the above described method of approximating the reception wave at each lattice point by the ambient sound velocity cannot cope with the unsteadiness of the sound velocity.

SUMMARY OF THE INVENTION

The present invention has been made in view of the above circumstances, and the object thereof is to provide an ultrasonic diagnosis apparatus and an ultrasonic diagnosis method which can determine a local sound velocity with high precision even where the sound velocity in an object is not uniform, and the reception time at each lattice cannot be approximated by the ambient sound velocity.

To achieve the above object, a first aspect of the present invention provides an ultrasonic diagnosis apparatus including: an ultrasonic probe which includes a plurality of ultrasonic transducers which transmit ultrasonic waves to an object, receive the ultrasonic waves reflected by the object, and output ultrasonic detection signals; a reception time calculating device which calculates at least one of a reception time and a reception wave at each of elements corresponding to lattice points set in a shallower region than a region of interest in the object; an image generating device which generates an image at a lattice point in the region of interest, based on a hypothetical sound velocity set in the region of interest and the calculated one of the reception time and the reception wave; an image analyzing device which analyzes the generated image; and a local sound velocity calculating device which calculates a local sound velocity in the region of interest, based on a result of the image analysis.

With this structure, reception times are determined, and a local sound velocity is then calculated based on the reception times. Accordingly, even where the sound velocity in the object is not uniform, a local sound velocity can be calculated with high precision.

According to a second aspect of the invention, the reception time calculating device calculates the reception time, using an image analysis technique and a phase aberration analysis technique.

With this structure, reception times can be readily calculated.

According to a third aspect of the present invention, the image generating device generates a combined reception wave by combining the reception waves of the lattice points set in the shallower region with a delay determined by the hypothetical sound velocity, and generates the image based on a delay generated from the combined reception wave.

With this structure, an image is generated from a combined reception wave, and a local sound velocity is determined by analyzing the image. Accordingly, a local sound velocity can be determined with higher precision.

According to a fourth aspect of the present invention, the image generating device determines a delay at the ultrasonic probe, and generates the image based on the delay at the ultrasonic probe, the delay at the ultrasonic probe being the smallest value of sums with respect to the ultrasonic probe, each of the sums being the sum of a propagation period determined from a hypothetical sound velocity set in the region of interest and the reception time at one of the lattice points set in the shallower region, the propagation period being a period for propagation from the lattice point in the region of interest to the one of the lattice points set in the shallower region.

According to a fifth aspect of the present invention, the ultrasonic diagnosis apparatus according to the first or second aspect of the present invention further includes a matching and adding device which regards the lattice points set in the shallower region as virtual elements, and matches and adds reception signals of the virtual elements. In this ultrasonic diagnosis apparatus, the image generating device generates the image at the lattice point in the region of interest from the reception signals of the virtual elements, based on the hypothetical sound velocity set in the region of interest.

With this structure, reception times are determined, and a local sound velocity is calculated based on the reception times. Accordingly, even where the sound velocity in the object is not uniform, a local sound velocity can be calculated with high precision.

According to a sixth aspect of the present invention, the matching and adding device sets a signal formed by matching and adding the reception signals of the respective virtual elements, with the reception time at each element being a delay.

According to a seventh aspect of the present invention, the image analyzing device calculates a sharpness value in the image, and the local sound velocity calculating device calculates the local sound velocity which is the hypothetical sound velocity corresponding to the image having the largest sharpness value.

To also achieve the above object, an eighth aspect of the present invention provides an ultrasonic diagnosis method including: transmitting ultrasonic waves to an object, and outputting ultrasonic detection signals after receiving the ultrasonic waves reflected by the object; calculating at least one of a reception time and a reception wave at each of elements corresponding to lattice points set in a shallower region than a region of interest in the object; generating an image at a lattice point in the region of interest, based on a hypothetical sound velocity set in the region of interest and the calculated one of the reception time and the reception wave; analyzing the generated image; and calculating a local sound velocity in the region of interest, based on the result of the image analysis.

By this method, reception times are determined, and a local sound velocity is then calculated based on the reception times. Accordingly, even where the sound velocity in the object is not uniform, a local sound velocity can be calculated with high precision.

According to a ninth aspect of the present invention, the calculating the reception time includes using an image analysis technique and a phase aberration analysis technique to calculate the reception time.

By this method, reception times can be readily calculated.

According to a tenth aspect of the present invention, the generating the image includes generating a combined reception wave by combining the reception waves of the lattice points set in the shallower region with a delay determined by the hypothetical sound velocity, and the generating the image includes generating the image based on a delay generated from the combined reception wave.

According to an eleventh aspect of the present invention, the generating the image includes determining a delay at the ultrasonic probe, and generating the image based on the delay at the ultrasonic probe, the delay at the ultrasonic probe being the smallest value of sums with respect to the ultrasonic probe, each of the sums being the sum of a propagation period determined from a hypothetical sound velocity set in the region of interest and the reception time at one of the lattice points set in the shallower region, the propagation period being a period for propagation from the lattice point in the region of interest to the one of the lattice points set in the shallower region.

According to a twelfth aspect of the present invention, the ultrasonic diagnosis method according to the eighth or ninth aspect of the present invention further includes matching and adding reception signals of respective virtual elements which are the lattice points set in the shallower region. In this ultrasonic diagnosis method, the generating the image includes generating the image at the lattice point in the region of interest from the reception signals of the virtual elements, based on the hypothetical sound velocity set in the region of interest.

By this method, a local sound velocity can be determined with high precision, even where the sound velocity in the object is not uniform.

According to a thirteenth aspect of the present invention, the matching and adding the reception signals includes setting a signal formed by matching and adding the reception signals of the respective virtual elements, with the reception time at each element being a delay.

According to a fourteenth aspect of the present invention, the analyzing the image includes calculating a sharpness value in the image, and the calculating the local sound velocity includes calculating the local sound velocity which is the hypothetical sound velocity corresponding to the image having the largest sharpness value.

This method according to the present invention may be embodied on a non-transitory computer-readable medium.

As described above, according to the present invention, the reception time or the reception wave of each of elements corresponding to respective lattices is determined, and a local sound velocity is calculated based on the reception times or the reception waves. Accordingly, even where the sound velocity in the object is not uniform, a local sound velocity can be determined with high precision.

DETAILED DESCRIPTION OF THE PREFERRED EMBODIMENTS

The following is a detailed description of ultrasonic diagnosis apparatuses and ultrasonic diagnosis methods according to the present invention, with reference to the accompanying drawings.

Figure 1:
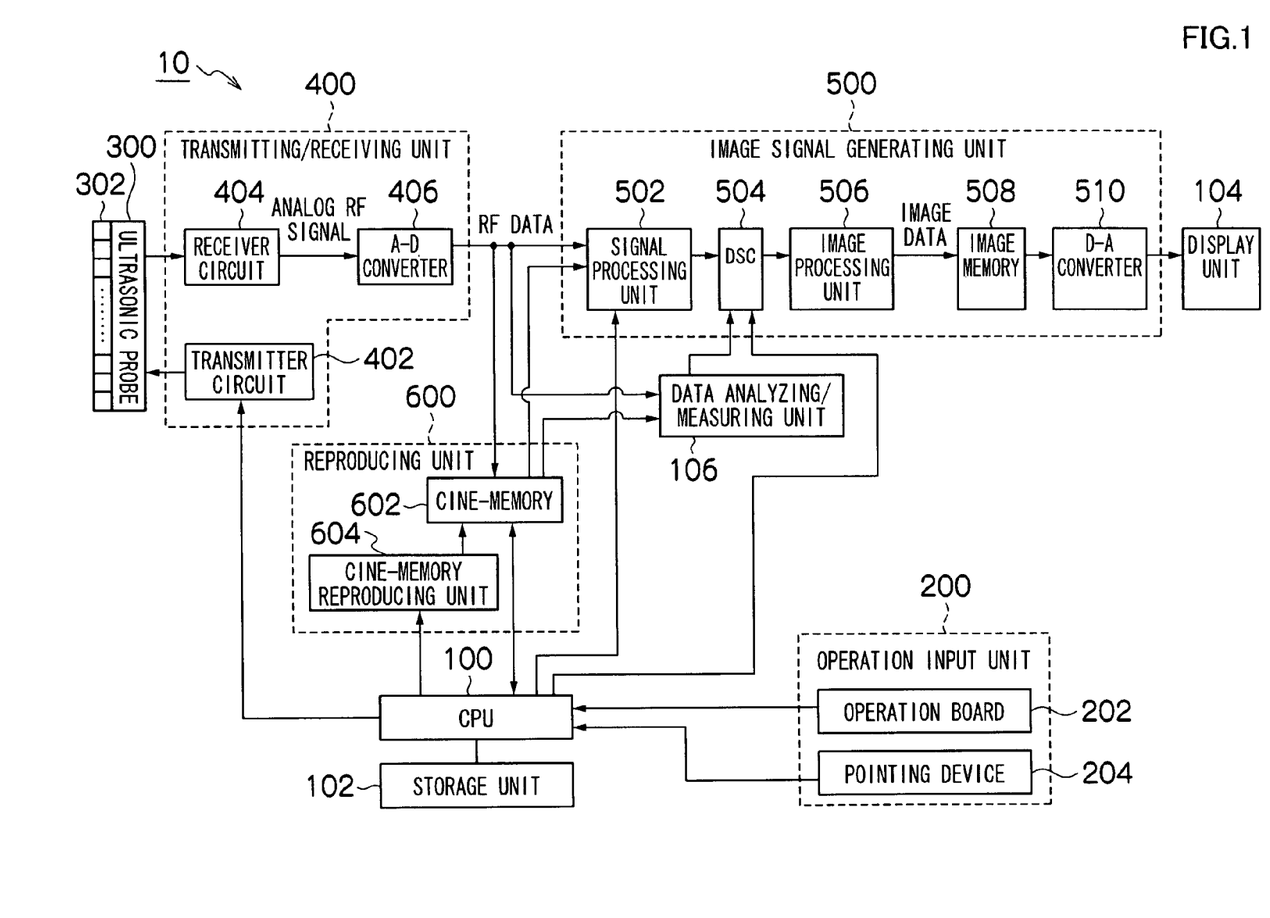
FIG. 1 is a block diagram schematically showing the structure of an ultrasonic diagnosis apparatus according to an embodiment of the present invention.

FIG. 1 is a block diagram schematically showing the structure of an ultrasonic diagnosis apparatus according to an embodiment of the present invention.

As shown in FIG. 1, the ultrasonic diagnosis apparatus 10 of this embodiment transmits ultrasonic beams from an ultrasonic probe 300 to an object OBJ, receives ultrasonic beams reflected by the object OBJ (ultrasonic echoes), and creates and displays an ultrasonic image based on ultrasonic echo detection signals.

A CPU (Central Processing Unit) 100 controls respective blocks of the ultrasonic diagnosis apparatus 10, in accordance with operations input through an operation input unit 200.

The operation input unit 200 is an input device which receives operations input from an operator, and includes an operation board 202 and a pointing device 204. The operation board 202 includes a keyboard which receives inputs of textual information (patient information, for example), a display mode switching button which switches the display mode between a mode for displaying only an amplitude image (a B-mode image) and a mode for displaying a result of determination made on the value of the local sound velocity, a freeze button for issuing an instruction to switch a mode between a live mode and a frozen mode, a cine-memory reproduction button for issuing an instruction to reproduce a cine-memory, and an analysis/measurement button for issuing an instruction to analyze/measure an ultrasonic image. The pointing device 204 is a device which receives inputs of designation of a region on the screen of a display unit 104, and may be a trackball or a mouse, for example. Alternatively, a touch panel may be used as the pointing device 204, for example.

A storage unit 102 is a storage device which stores the control program for the CPU 100 to control the respective blocks of the ultrasonic diagnosis apparatus 10, and may be a hard disk or a semiconductor memory, for example.

A display unit 104 may be a CRT (Cathode Ray Tube) display or a liquid crystal display, and displays an ultrasonic image (a video image or a still image) and various kinds of setting screens.

The ultrasonic probe 300 is a probe which is in contact with object OBJ when used, and includes ultrasonic transducers 302 which constitute a one- or two-dimensional transducer array. The ultrasonic transducers 302 transmit ultrasonic beams to the object OBJ, based on a drive signal applied from a transmitter circuit 402. The ultrasonic transducers 302 then receive ultrasonic echos reflected from the object OBJ, and output detection signals.

The ultrasonic transducers 302 include oscillators. Each of the oscillators is formed by providing electrodes at both ends of a material having piezoelectric properties (a piezoelectric material). Examples of piezoelectric materials forming such oscillators include piezoelectric ceramics such as PZT (Pb (lead) zirconate titanate) and polymer piezoelectric element such as PVDF (polyvinylidene difluoride). When an electric signal is sent to the electrodes of the oscillators, the piezoelectric material expands and contracts, and ultrasonic waves are generated in each oscillator by the expansion and contraction of the piezoelectric material. For example, where a pulsed electric signal is sent to the electrodes of the oscillators, pulsed ultrasonic waves are generated. Where a continuous-wave electric signal is sent to the electrodes of the oscillators, continuous ultrasonic waves are generated. The ultrasonic waves generated in the respective oscillators are combined to form an ultrasonic beam. Also, when the ultrasonic waves are received by the respective oscillators, the piezoelectric material of each oscillator expands and contracts, to generate an electric signal. The electric signals generated in the respective oscillators are output as ultrasonic detection signals to a receiver circuit 404.

It should be noted that two or more kinds of elements of different ultrasonic transduction types can be used as the ultrasonic transducers 302. For example, oscillators formed by the above described piezoelectric material may be used as elements which transmit ultrasonic waves, and ultrasonic transducers of a photodetection type may be used as the elements which receive ultrasonic waves. Here, the ultrasonic transducers of a photodetection type perform a detecting operation by converting an ultrasonic signal into an optical signal, and such ultrasonic transducers may be Fabry-Perot resonators or fiber Bragg lattices, for example.

Next, an ultrasonic diagnosing process to be performed in the live mode is described. The live mode is a mode in which an ultrasonic image (a video image) obtained by bringing the ultrasonic probe 300 into contact with the object OBJ and performing transmission/reception of ultrasonic waves is displayed and analyzed/measured.

When the ultrasonic probe 300 is brought into contact with the object OBJ, and ultrasonic diagnosing is started in accordance with an instruction input through the operation input unit 200, the CPU 100 outputs a control signal to a transmitting/receiving unit 400, to cause the transmitting/receiving unit 400 to start transmission of ultrasonic beams to the object OBJ and reception of ultrasonic echoes from the object OBJ. The CPU 100 sets an ultrasonic beam transmitting direction and an ultrasonic echo receiving direction for each ultrasonic transducer 302.

Further, the CPU 100 selects a transmission delay pattern in accordance with the ultrasonic beam transmitting direction, and selects a reception delay pattern in accordance with the ultrasonic echo receiving direction. Here, a transmission delay pattern is delay time pattern data to be supplied to the drive signal, so as to form ultrasonic beams in a desired direction with ultrasonic waves transmitted from two or more ultrasonic transducers 302. A reception delay pattern is delay time pattern data to be received by two or more ultrasonic transducers 302. Such transmission delay patterns and reception patterns are stored beforehand into the storage unit 102. The CPU 100 selects a transmission delay pattern and a reception delay pattern from those stored in the storage unit 102. In accordance with the selected transmission delay pattern and reception delay pattern, the CPU 100 outputs the control signal to the transmitting/receiving unit 400, to control transmission and reception of ultrasonic waves.

In accordance with the control signal from the CPU 100, the transmitter circuit 402 generates the drive signal, and applies the drive signal to the ultrasonic transducers 302. At this point, based on the transmission delay pattern selected by the CPU 100, the transmitter circuit 402 delays the drive signal to be applied to each of the ultrasonic transducers 302. Here, the transmitter circuit 402 performs a transmit focusing process to adjust (delay) the timing to apply the drive signal to each of the ultrasonic transducers 302, so that the ultrasonic waves transmitted from the respective ultrasonic transducers 302 form ultrasonic beams. Alternatively, the timing to apply the drive signal may be adjusted so that the ultrasonic waves simultaneously transmitted from two or more ultrasonic transducers 302 reach the entire imaging region of the object OBJ.

The receiver circuit 404 receives and amplifies the ultrasonic detection signals output from the respective ultrasonic transducers 302. As described above, the distances between the respective ultrasonic transducers 302 and the ultrasonic reflection source $X_{ROI}$ in the object OBJ vary. Therefore, the periods of time required for a reflected wave to reach the respective ultrasonic transducers 302 vary. The receiver circuit 404 includes a delay circuit. In accordance with a sound velocity (hereinafter referred to as a hypothetical sound velocity) which is set based on the reception delay pattern selected by the CPU 100 or the distribution of velocities of sound, the receiver circuit 404 delays each detection signal by the amount equivalent to the difference (delay time) in arrival time of the reflected wave. The receiver circuit 404 then performs a receive focusing operation by matching and adding up the detection signals having the delay times added thereto. If another ultrasonic reflection source exists at a different location from the ultrasonic reflection source $X_{ROI}$, the arrival times of ultrasonic detection signals from the other ultrasonic reflection source differ from those of the ultrasonic detection signals from the ultrasonic reflection source $X_{ROI}$. Therefore, the phases of the ultrasonic detection signals from the other ultrasonic reflection source are cancelled by adding up the detection signals at the adding circuit of the receiver circuit 404. In this manner, the reception signal from the ultrasonic reflection source $X_{ROI}$ becomes the largest, and focusing is achieved. Through the above receive focusing operation, an acoustic ray signal (hereinafter referred to as the RF signal) with ultrasonic echoes having the narrowed focuses is formed.

The A-D converter 406 converts the analog RF signal output from the receiver circuit 404 into a digital RF signal (hereinafter referred to as RF data). Here, the RF data contains phase information about received waves (carrier waves). The RF data output from the A-D converter 406 is input to a signal processing unit 502 and a cine-memory 602.

The cine-memory 602 sequentially stores the RF data input from the A-D converter 406. The cine-memory 602 also stores and associates information about frame rates input from the CPU 100 (the parameters indicating the depth of the reflection location of ultrasonic waves, the scanning line density, and the width of the field of view, for example) with the above described RF data.

For the RF data, the signal processing unit 502 performs STC (Sensitivity Time gain Control) to correct attenuations caused by distances in accordance with the depth of the reflection location of ultrasonic waves. After that, the signal processing unit 502 performs an envelope detecting operation to generate B-mode image data (image data in which the amplitudes of ultrasonic echoes are represented by the brightness (luminance) of dots).

The B-mode image data generated by the signal processing unit 502 is obtained by a different scanning technique from a conventional television signal scanning technique. Therefore, a DSC (Digital Scan Converter) 504 converts (raster-converts) the B-mode image data into conventional image data (image data according to the television signal scanning system (the NTSC system), for example). An image processing unit 506 performs various kinds of necessary image processing (gradation processing, for example) on the image data input from the DSC 504.

The image memory 508 stores the image data input from the image processing unit 506. A D-A converter 510 converts the image data read from the image memory 508 into an analog image signal, and outputs the analog image signal to the display unit 104. In this manner, an ultrasonic image (a video image) captured by the ultrasonic probe 300 is displayed on the display unit 104.

In this embodiment, detection signals subjected to the receive focusing operation at the receiver circuit 404 are RF signals. However, detection signals having not been subjected to a receive focusing operation may be used as RF signals. In that case, the ultrasonic detection signals output from the ultrasonic transducers 302 are amplified at the receiver circuit 404, and the amplified detection signals or the RF signals are A-D converted by the A-D converter 406 to generate RF data. The RD data is supplied to the signal processing unit 502, and is also stored into the cine-memory 602. The receive focusing operation is digitally performed at the signal processing unit 502.

Next, the cine-memory reproduction mode is described. The cine-memory reproduction mode is a mode in which an ultrasonic diagnosis image is displayed and analyzed/measured, based on the RF data stored in the cine-memory 602.

When the cine-memory reproduction button of the operation board 202 is pressed, the CPU 100 switches the operation mode of the ultrasonic diagnosis apparatus 10 to the cine-memory reproduction mode. In the cine-memory reproduction mode, the CPU 100 instructs a cine-memory reproducing unit 604 to reproduce RF data designated by an operation input from an operator. Based on the instruction from the CPU 100, the cine-memory reproducing unit 604 reads the RF data from the cine-memory 602, and transmits the RF data to the signal processing unit 502 of the image signal generating unit 500. The RF data transmitted from the cine-memory 602 is subjected to predetermined processing (similar processing as that performed in the live mode) at the signal processing unit 502, the DSC 504, and the image processing unit 506, and is converted into image data. The image data is then output to the display unit 104 via the image memory 508 and the D-A converter 501. In this manner, the ultrasonic image (a video image or a still image) based on the RF data stored in the cine-memory 602 is displayed on the display unit 104.

In either one of the live mode and the cine-memory reproduction mode, when the freeze button of the operation board 202 is pressed while an ultrasonic image (a video image) is being displayed, the ultrasonic image being displayed at the time of the pressing of the freeze button is turned into a still image on the display unit 104. Accordingly, the operator can observe the still image displayed in the region of interest (ROI).

When the analysis/measurement button of the operation board 202 is pressed, an analyzing/measuring operation designated by an operation input from the operator is performed. Where the analysis/measurement button is pressed in each operation mode, a data analyzing/measuring unit 106 obtains RF data having not subjected to image processing from the A-D converter 406 or the cine-memory 602, and performs the analyzing/measuring operation (an analysis of deformation of a tissue site (hardness diagnosing), a measurement of a bloodstream, a measurement of movement of a tissue site, or a measurement of an IMT (Intima-Media Thickness) value, for example) designated by the operator with the use of the RF data. The data analyzing/measuring unit 106 also performs an operation to measure the value of a local sound velocity, which will be described later in detail. The results of the analysis/measurement carried out by the data analyzing/measuring unit 106 are output to the DSC 504 of the image signal generating unit 500. The DSC 504 inserts the analysis/measurement results from the data analyzing/measuring unit 106 into the image data of an ultrasonic image, and outputs the image data having the results inserted thereinto to the display unit 104. In this manner, the ultrasonic image and the analysis/measurement results are displayed on the display unit 104.

When the display mode switching button is pressed, the display mode is switched between a mode to display only a B-mode image, a mode to superimpose the result of determination of the value of a local sound velocity upon the B-mode image (a display which changes color coding or luminance in accordance with the value of the local sound velocity, or a display which connects the dots having the same value of the local sound velocity), and a mode to display the B-mode image in line with an image of the result of determination of the value of the local sound velocity. Accordingly, the operator can spot a pathological lesion by observing the result of determination of the value of the local sound velocity.

Based on the result of determination of the value of the local sound velocity, at least one of a transmit focus operation and a receive focus operation may be performed to obtain a B-mode image, and the B-mode image may be displayed on the display unit 104.

In the following, the functions of the ultrasonic diagnosis apparatus 10 of this embodiment are described.

The present invention enables a measurement of a local sound velocity even where the sound velocity in an object is not uniform and the reception time (or reception wave) at each of the elements corresponding to respective lattices cannot be approximated by the ambient sound velocity.

Figure 2:
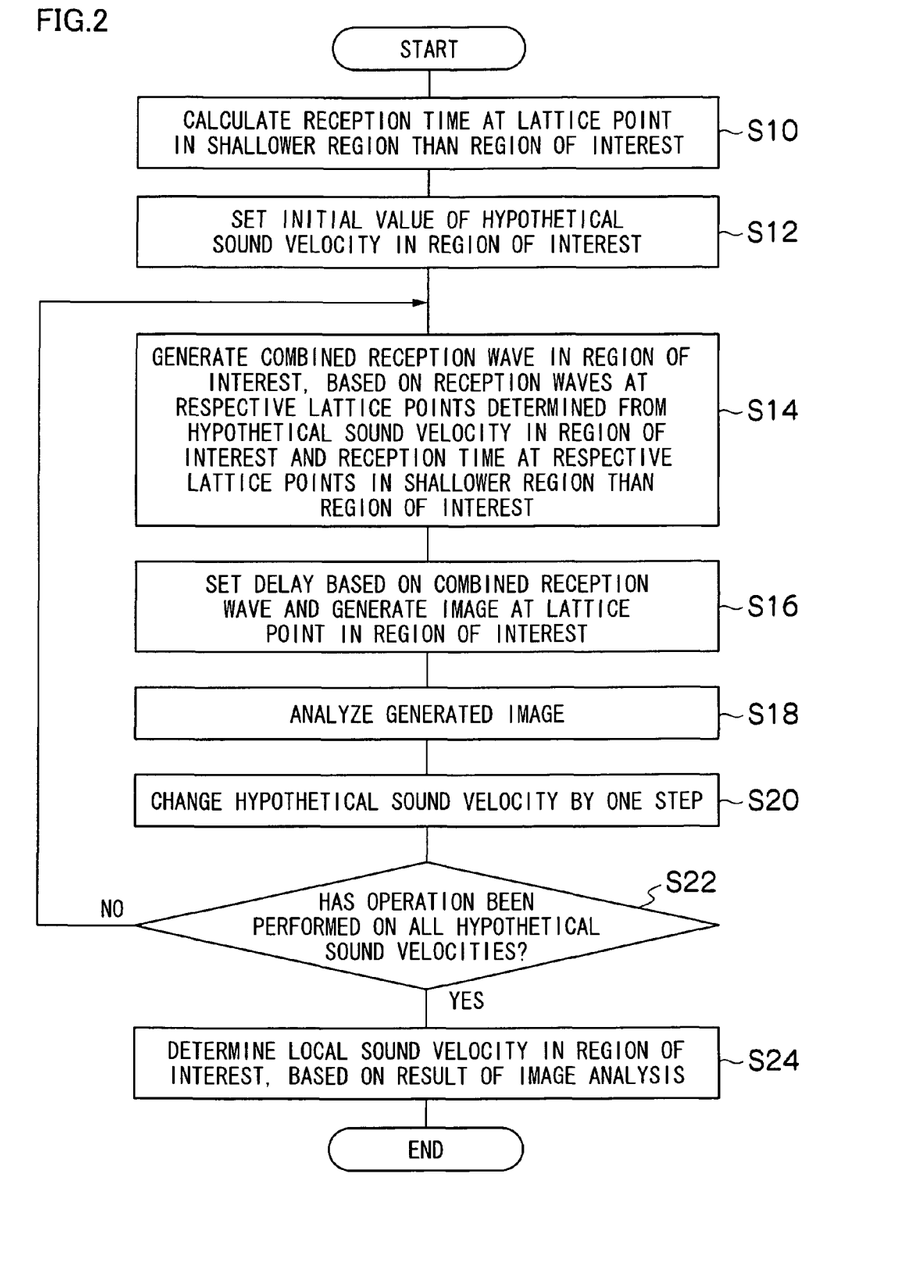
FIG. 2 is a flowchart showing an operation according to a first embodiment of the present invention.

Referring now to the flowchart shown in FIG. 2, a first embodiment of the present invention is described. Hereinafter, the blocks of flowcharts represent computer-readable instructions read from a non-transitory computer-readable medium such as the storage unit 102, for directing the CPU 100 to execute the following steps.

The first embodiment is to determine a local sound velocity by determining the reception times (or reception waves) at lattice points (grid points) in a shallower region than the region of interest, combining the reception times with delays determined by the hypothetical sound velocity in the region of interest, generating an image based on a delay generated from the combination, and analyzing the image. In the embodiment described below, to determine the local sound velocity in the region of interest with the use of the reception time or reception wave at each of elements corresponding to the respective lattices, the reception time at each element is first determined, and the reception wave of each element is then determined as needed. Alternatively, the reception wave of each element may be first determined, and the reception time at each element is then determined as needed. To determine the reception wave at each of the elements, scattering is reduced by subjecting each of the lattices to a transmit focus, and only the signal formed by receiving the reflection from each of the lattice should be used.

Figure 3:
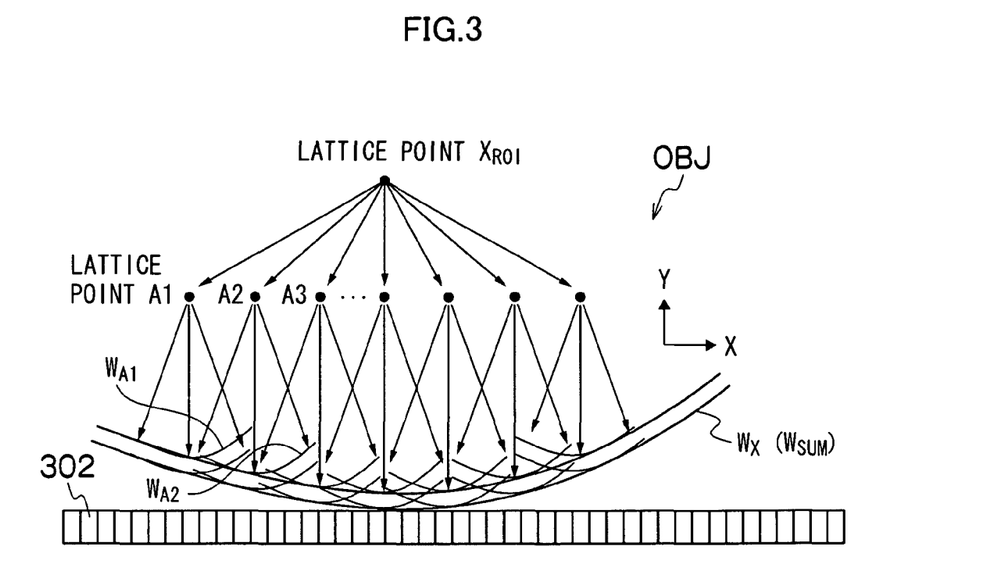
FIG. 3 is a schematic view illustrating an operation to calculate the value of a local sound velocity according to the first embodiment.

FIG. 3 schematically shows an operation to calculate the value of a local sound velocity according to this embodiment.

As shown in FIG. 3, a representative lattice point in a region of interest ROI in the object OBJ is represented by $X_{ROI}$, and the lattice points arranged at regular intervals in the X-Y direction in shallower positions than the lattice point $X_{ROI}$ (or in positions close to the ultrasonic transducers 302) are represented by A1, A2, A3, . . . . The sound velocities at least between the lattice point $X_{ROI}$ and the respective lattice points A1, A2, A3, . . . are assumed to be uniform. Here, the range and the number of lattice points A1, A2, A3, . . . to be used in the operation to determine the value of the local sound velocity in the region of interest are determined in advance.

First, in step S10 of FIG. 2, the reception times at the lattice points A1, A2, A3, . . . located in a shallower region than the region of interest are calculated. The reception times at the respective lattice points A1, A2, and A3, . . . can be calculated by a known image analysis method and a known phase aberration analysis method.

The image analysis method used herein is a method of hypothetically setting the mean sound velocity (and depth) and determining such a value that the characteristics such as the sharpness and contrast of the image of the sound source are maximized, as disclosed in Japanese Patent Application Laid-Open No. 2007-2045 and the like.

The phase aberration analysis method is disclosed in Japanese Patent Application Laid-Open No. 6-105841 and the like. According to this method, a signal is set as a reference signal for reception signals of the respective elements of an ultrasonic probe, and the phase differences between the reference signal and the reception signals are detected. The phase difference detection results of each two adjacent elements are compared, and the difference between the results is represented by D. In a graph which plots the device number on the abscissa axis, and plots the phase differences between the reference signal S and the reception signals of the respective elements on the ordinate axis, 360 degrees is added at discontinuous points from positive to negative (or when the above described difference D is smaller than −180 degrees), and 360 degrees is subtracted at discontinuous points from negative to positive (or when the above described difference D is larger than 180 degrees). In this manner, discontinuous curves are turned into continuous curves, and thus, the phase aberration in a wide region is detected with high precision.

In step S12 of FIG. 2, the initial value of a hypothetical sound velocity in the region of interest is set.

In step S14, a combined reception wave at the lattice point $X_{ROI}$ is formed by overlapping the reception waves of the respective lattices on one another with the use of delays determined by the hypothetical sound velocity in the region of interest.

That is, the combined reception wave $W_{SUM}$ from the lattice point $X_{ROI}$ is formed with the use of the reception waves $W_{A1}$, $W_{A2}$, ... from the lattice points A1, A2, A3, ... and the delays obtained from the hypothetical sound velocity, as shown in FIG. 3.

In step S16, a delay is set by the combined reception wave, and an image at the lattice point $X_{ROI}$ in the region of interest is generated based on the delay. The method of generating the delay from the combined reception wave is as follows. An equiphase line is extracted from the phase differences in the combined reception wave between adjacent elements, and the equiphase line is set as the delay. Alternatively, the phase difference in the maximum (peak) position of the combined reception wave between the respective elements may be set as the delay. Alternatively, the cross-correlation peak position of the combined reception wave from each element may be set as the delay.

In step S18, the image generated at the lattice point $X_{ROI}$ in the region of interest is analyzed. In analyzing the image, the sharpness value in the image is calculated, for example.

In step S20 the hypothetical velocity is changed by one step. In step S22, a check is made to determine whether the operation has been performed on all the hypothetical sound velocities. It should be noted that the range of hypothetical sound velocities to be subjected to the operation is determined in advance.

If the operation has not been performed on all the hypothetical sound velocities, the operation returns to step S14, and the above described procedures are repeated.

In a case where the operation has been performed on all the hypothetical sound velocities, the operation moves on to step S24, and the value of the local sound velocity in the region of interest is determined. In doing so, the value of the local sound velocity in the region of interest is determined from the hypothetical sound velocity at which the sharpness value in the image is the largest, as a result of repetitions of the above described procedures.

The method of determining the value of the local sound velocity in the region of interest from the hypothetical sound velocity at which the sharpness value in the image becomes the largest is not limited to a particular method. For example, in the above repeated procedures of steps S14 through S22, the sharpness value in an image is calculated, and is compared with the previous calculated sharpness value. The hypothetical sound velocity corresponding to the image having the larger sharpness value is stored. When the operation on all the hypothetical sound velocities is finished, the hypothetical sound velocity still stored is set as the local sound velocity.

Figure 4:
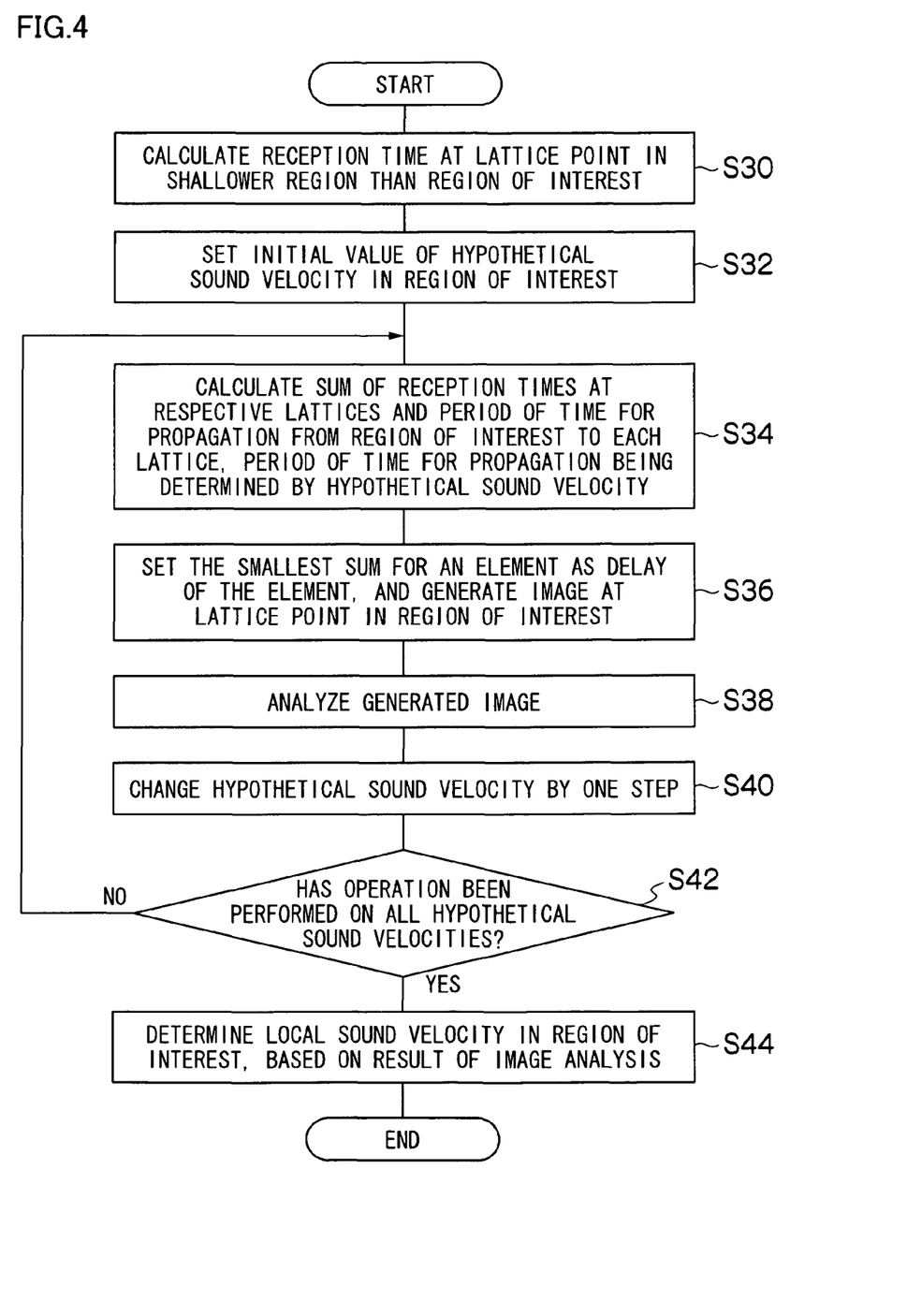
FIG. 4 is a flowchart showing an operation according to a second embodiment of the present invention.

Referring now to the flowchart shown in FIG. 4, a second embodiment of the present invention is described.

The second embodiment is to determine a local sound velocity by determining the reception times (or reception waves) at lattice points in a shallower region than the region of interest, calculating the sum of the period of time for propagation from the region of interest to each of the lattice points determined by a hypothetical sound velocity in the region of interest and the reception time of each corresponding one of the lattice points, setting the smallest value of the sums as the delay at the element, generating an image based on the delay, and analyzing the image.

Figure 5:
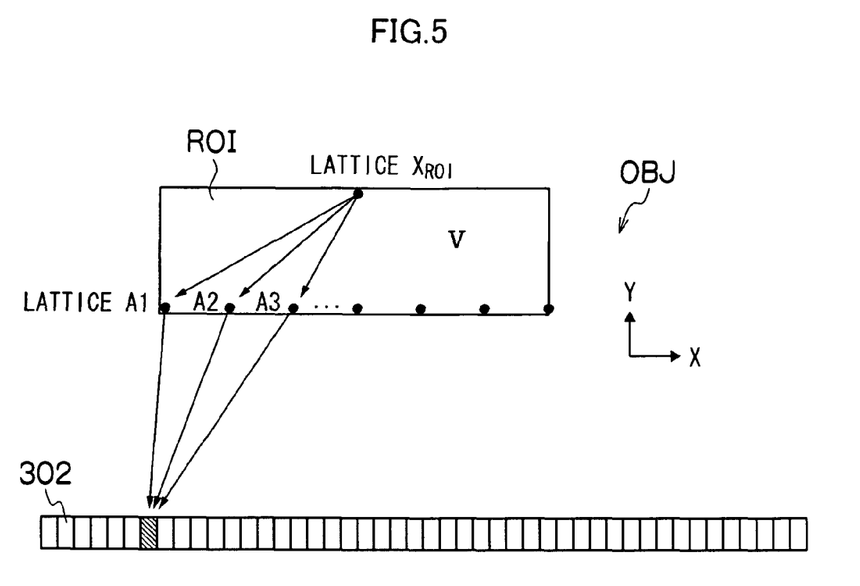
FIG. 5 is a schematic view illustrating an operation to calculate the value of a local sound velocity according to the second embodiment of the present invention.

FIG. 5 schematically shows an operation to calculate the value of a local sound velocity according to this embodiment.

In FIG. 5, a representative lattice point in the region of interest ROI in the object OBJ is represented by $X_{ROI}$, and the lattice points arranged at regular intervals in the X-Y direction in shallower positions than the lattice point $X_{ROI}$ (or in positions close to the ultrasonic transducers 302) are represented by A1, A2, A3, ..., as in FIG. 3. The sound velocities at least between the lattice point $X_{ROI}$ and the respective lattice points A1, A2, A3, ... are assumed to be uniform. Here, the range and the number of lattice points A1, A2, A3, ... to be used in the operation to determine the value of the local sound velocity in the region of interest are determined in advance.

First, in step S30 of FIG. 4, the reception times at the lattice points A1, A2, A3, ... located in a shallower region than the region of interest are calculated. The reception times at the respective lattice points A1, A2, and A3, ... can be calculated by a known image analysis method and a known phase aberration analysis method, as in the first embodiment.

In step S32, the initial value of the hypothetical sound velocity in the region of interest is set. In step S34, the periods for propagation from the region of interest to the respective lattices which are determined by hypothetical sound velocities and the respective lattice reception times are added up to calculate a combined reception time.

That is, the periods for propagation from the region of interest (the lattice point $X_{ROI}$) to the respective lattice points A1, A2, A3, ... are calculated from hypothetical sound velocities set in the region of interest ROI, and the sum of the propagation periods of time and the already determined reception times at the respective lattice points A1, A2, A3, ... is calculated.

Where the hypothetical sound velocity in the region of interest ROI is represented by V, the periods for propagation from the lattice point $X_{ROI}$ to the respective lattice points A1, A2, A3, ... are calculated from $X_{ROI}A1/V$, $X_{ROI}A2/V$, $X_{ROI}A3/V$, ..., respectively. Here, $X_{ROI}A1$, $X_{ROI}A2$, $X_{ROI}A3$, ... represent the distances from the lattice point $X_{ROI}$ to the respective lattice points A1, A2, A3, ..., and can be calculated to be $\sqrt{(\Delta X_{A1}^2+\Delta Y^2)}$, $\sqrt{(\Delta X_{A2}^2+\Delta Y^2)}$, $\sqrt{(\Delta X_{A3}^2+\Delta Y^2)}$, ... from the depth-direction width $\Delta Y$ of the region of interest ROI and the X-direction distances $\Delta X_{A1}$, $\Delta X_{A2}$, $\Delta X_{A3}$, ... between the lattice point $X_{ROI}$ and the respective lattice points A1, A2, A3, ..., according to the Pythagorean theorem. Meanwhile, $\Delta Y$ can be calculated to be $\Delta Y=\Delta T*V/2$ from V and the depth-direction time width $\Delta T$ of the region of interest ROI (the difference between the reception time at the lattice point $X_{ROI}$ and the reception time at the element immediately below the lattice point An located immediately below the lattice point $X_{ROI}$ or the shortest reception time).

Since the reception times at the respective lattice points A1, A2, A3, ... have already been calculated, the sums of the periods for propagation from the region of interest to the respective lattices and the respective lattice reception times can be calculated to obtain combined reception times.

In step S36, the shortest combined reception time of the above combined reception times is determined with respect to an element (that is, the path which minimizes the period for propagation is determined among the paths extending from the lattice point $X_{ROI}$ to the element via a lattice point $A_k$ (deflecting at $A_k$)), and the shortest combined reception time is set as the delay of the element. Based on the delay, an image at the lattice point $X_{ROI}$ in the region of interest is generated.

In step S38, the generated image is analyzed. An image analysis is carried out in the similar manner as in step S18 of FIG. 2, and the sharpness value in the image is calculated, for example.

In step S40, the hypothetical sound velocity is changed by one step. In step S42, a check is made to determine whether the operation has been performed on all the hypothetical sound velocities. It should be noted that the range of hypothetical sound velocities to be subjected to the operation is determined in advance.

As a result, in a case where the operation has not been performed on all the hypothetical sound velocity, the operation returns to step S34, and the above described procedures are repeated.

In a case where the operation has been performed on all the hypothetical sound velocities, the value of the local sound velocity in the region of interest is determined in the next step S44. The determination of the value of the local sound velocity is performed in the similar manner as in the above described first embodiment.

Figure 6:
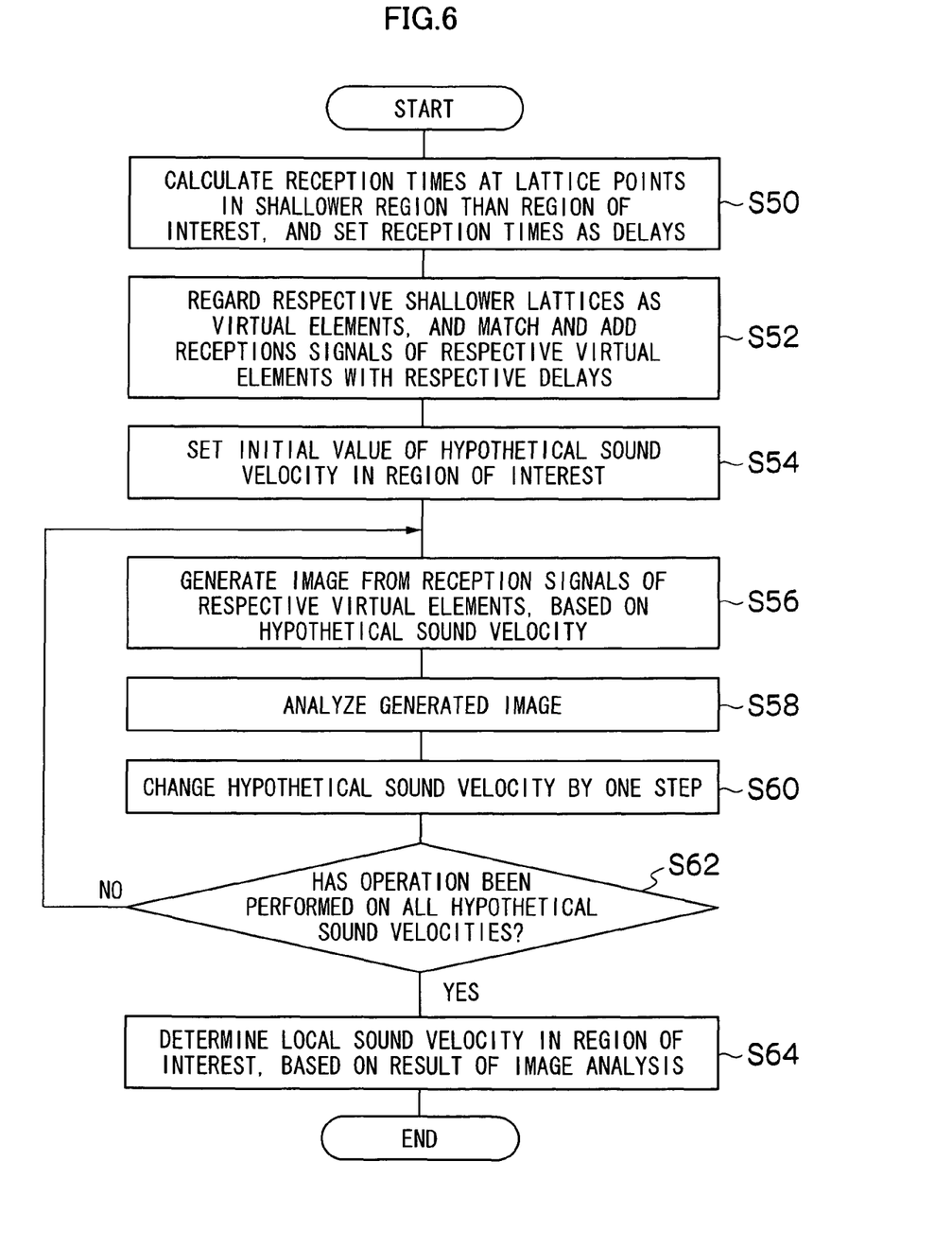
FIG. 6 is a flowchart showing an operation according to a third embodiment of the present invention.

Referring now to the flowchart shown in FIG. 6, a third embodiment of the present invention is described.

The third embodiment is to determine a local sound velocity by determining reception times at lattice points in a shallower region than the region of interest, setting the reception times as delays, regarding the lattice points in the shallower region as virtual elements, matching and adding reception signals of the respective virtual elements with the respective delays, generating an image based on the hypothetical sound velocity in the region of interest, and analyzing the image.

In this embodiment, a representative lattice point $X_{ROI}$ in the region of interest ROI in the object OBJ and shallower lattice points A1, A2, A3, . . . than the lattice point $X_{ROI}$ are set, as in the above described embodiments as shown in FIG. 3, for example. The sound velocities at least between the lattice point $X_{ROI}$ and the respective lattice points A1, A2, A3, . . . are assumed to be uniform.

First, in step S50, reception times at the respective lattice points A1, A2, A3, . . . located in a shallower region than the region of interest are calculated, and the reception times are set as delays. The reception times at the respective lattice points A1, A2, A3, . . . can be calculated by a known image analysis method and a known phase aberration analysis method as in the above described first embodiment.

In step S52, the respective lattices in the shallower region are regarded as virtual elements, and reception signals of the respective lattices are matched and added as the reception signals of the virtual elements with the above delays, to set the signal subjected to the matching and adding.

In step S54, the initial value of a hypothetical sound velocity in the region of interest is set.

In step S56, an image is generated from the reception signals of the respective virtual elements, based on the hypothetical sound velocity in the region of interest.

In step S58, the generated image is analyzed in the similar manner as in step S18 of FIG. 2, for example, and the sharpness value in the image is calculated, for example.

In step S60, the hypothetical sound velocity is changed by one step. In step S62, a check is made to determine whether the operation has been performed on all the hypothetical sound velocities. It should be noted that the range of hypothetical sound velocities to be subjected to the operation is determined in advance.

As a result, in a case where the operation has not been performed on all the hypothetical sound velocities, the operation returns to step S56, and the above procedures are repeated.

In a case where the operation has been performed on all the hypothetical sound velocities, the value of the local sound velocity in the region of interest is determined in the next step S64. In determining the value of the local sound velocity, the value of the hypothetical sound velocity corresponding to the image having the largest sharpness value is determined to be the value of the local sound velocity, based on the results of the above image analyses.

In each of the above described embodiments, the local sound velocity in a region of interest can be calculated with higher precision by using not only the result of an image analysis carried out at one lattice point but also the results of image analyses carried out at lattice points arranged in the depth direction of the region of interest or two-dimensionally (or three dimensionally) in the region of interest, or using sharpness values. Here, the local sound velocity in the region of interest may be determined based not on the sharpness values determined at the respective lattice points but on the local sound velocities at the respective lattices.

Lattice points in a shallower region than the region of interest may not necessarily be set by the technique illustrated in FIGS. 3 and 5, but may be set on any curved surface located lower than the region of interest (or located on the side of the ultrasonic transducers 302). For example, lattice points may be set on the boundaries with tissues or lesions.

As described above, in each of the above described embodiments, instead of the ambient sound velocity, a reception time is calculated at each lattice point. Accordingly, a local reception time can be calculated with high precision even where the sound velocity in the object is not uniform.

Although ultrasonic diagnosis apparatuses and ultrasonic diagnosis methods according to the present invention have been described so far, the present invention is not limited to the above examples, and various changes and modifications may of course be made to them without departing from the scope of the invention.

What is claimed is:

1. An ultrasonic diagnosis apparatus comprising:
    an ultrasonic probe including a plurality of ultrasonic transducers configured to transmit ultrasonic waves to an object, receive the ultrasonic waves reflected by the object, and output ultrasonic detection signals;
    a reception time calculating device configured to calculate at least one of a reception time and a reception wave at each of the plurality of ultrasonic transducers corresponding to a shallower point of two or more points whose positions along a depth direction of the object are different from each other;
    an image generating device configured to generate an image at the two or more points, based on a hypothetical sound velocity set in a region including the two or more points and the calculated one of the reception time and the reception wave;
    an image analyzing device configure to perform an image analysis of the generated image; and
    a local sound velocity calculating device configured to calculate a local sound velocity in the region including the two or more points, based on a result of the image analysis.

2. The ultrasonic diagnosis apparatus according to claim 1, wherein the reception time calculating device calculates the reception time, using an image analysis technique and a phase aberration analysis technique.

3. The ultrasonic diagnosis apparatus according to claim 1, wherein the reception time calculating device calculates the reception wave, and the image generating device generates a combined reception wave by combining the reception waves of points set in a shallower region than the two or more points with a delay determined by the hypothetical sound velocity, and generates the image based on a delay generated from the combined reception wave.

4. The ultrasonic diagnosis apparatus according to claim 1, wherein the image generating device determines a delay at the ultrasonic probe, and generates the image based on the delay at the ultrasonic probe, the delay at the ultrasonic probe being the smallest value of sums with respect to the ultrasonic probe, each of the sums being a sum of a propagation period determined from a hypothetical sound velocity set in the region including the two or more points and the reception time at one of points set in a shallower region than the two or more points, the propagation period being a period for propagation from the point set in the region including the two or more points to the one of the points set in the shallower region.

5. The ultrasonic diagnosis apparatus according to claim 1, further comprising:
    a matching and adding device configured to match and add reception signals of virtual elements which are points set in a shallower region than the two or more points,
    wherein the image generating device generates the image at a point in the region including the two or more points from the reception signals of the virtual elements, based on the hypothetical sound velocity set in the region including the two or more points.

6. The ultrasonic diagnosis apparatus according to claim 5, wherein the reception time calculating device calculates the reception time, and the matching and adding device sets a signal formed by matching and adding the reception signals of the respective virtual elements, with the reception time at each element being a delay.

7. The ultrasonic diagnosis apparatus according to claim 1, wherein
    the image analyzing device calculates a sharpness value in the image, and
    the local sound velocity calculating device calculates the local sound velocity which is the hypothetical sound velocity corresponding to the image having the largest sharpness value.

8. An ultrasonic diagnosis method executed by an ultrasonic diagnosis apparatus, comprising:
    transmitting ultrasonic waves to an object, and outputting ultrasonic detection signals after receiving the ultrasonic waves reflected by the object;
    calculating at least one of a reception time and a reception wave at each of the plurality of ultrasonic transducers corresponding to a shallower point of two or more points whose positions along a depth direction of the object are different from each other;
    generating an image at the two or more points, based on a hypothetical sound velocity set in a region including the two or more points and the calculated one of the reception time and the reception wave;
    performing an image analysis of the generated image; and
    calculating a local sound velocity in the region including the two or more points, based on a result of the image analysis.

9. The ultrasonic diagnosis method according to claim 8, wherein the calculating the reception time includes using an image analysis technique and a phase aberration analysis technique to calculate the reception time.

10. The ultrasonic diagnosis method according to claim 8, wherein the calculating the reception time includes calculating the reception wave, and the generating the image includes generating a combined reception wave by combining the reception waves of points set in a shallower region than the two or more points with a delay determined by the hypothetical sound velocity, and the generating the image includes generating the image based on a delay generated from the combined reception wave.

11. The ultrasonic diagnosis method according to claim 8, wherein the generating the image includes determining a delay at the ultrasonic probe, and generating the image based on the delay at the ultrasonic probe, the delay at the ultrasonic probe being the smallest value of sums with respect to the ultrasonic probe, each of the sums being a sum of a propagation period determined from a hypothetical sound velocity set in the region including the two or more points and the reception time at one of the points set in a shallower region than the two or more points, the propagation period being a period for propagation from the point in the region including the two or more points to the one of the point set in the shallower region.

12. The ultrasonic diagnosis method according to claim 8, further comprising:
    matching and adding reception signals of respective virtual elements which are points set in a shallower region than the two or more points,
    wherein the generating the image includes generating the image at a point in the region including the two or more points from the reception signals of the virtual elements, based on the hypothetical sound velocity set in the region including the two or more points.

13. The ultrasonic diagnosis method according to claim 12, wherein the matching and adding includes setting a signal formed by matching and adding the reception signals of the respective virtual elements, with the reception time at each element being a delay.

14. The ultrasonic diagnosis method according to claim 8, wherein
    the analyzing the image includes calculating a sharpness value in the image, and
    the calculating the local sound velocity includes calculating the local sound velocity which is the hypothetical sound velocity corresponding to the image having the largest sharpness value.

15. A non-transitory computer-readable medium having embodied thereon instructions which executed by a ultrasonic diagnosis apparatus cause the ultrasonic diagnosis apparatus to perform a method comprising:
    transmitting ultrasonic waves to an object, and outputting ultrasonic detection signals after receiving the ultrasonic waves reflected by the object;
    calculating at least one of a reception time and a reception wave at each of the plurality of ultrasonic transducers corresponding to a shallower point of two or more points whose positions along a depth direction of the object are different from each other;
    generating an image at the two or more points, based on a hypothetical sound velocity set in a region including the two or more points and the calculated one of the reception time and the reception wave;
    performing an image analysis of the generated image; and
    calculating a local sound velocity in the region including the two or more points, based on a result of the image analysis.

16. The ultrasonic diagnosis apparatus according to claim 1, further comprising:
a transmission focusing device configured to perform different transmission focus of the ultrasound waves on each of the two or more points when the received signals are obtained from each of the two or more points.

17. The ultrasound diagnostic apparatus according to claim 1, wherein the image generating device obtains a delay based on a propagation time calculated based on hypothetical sound velocity set in the region including the two or more points and the reception time of the shallower points, and generates the image based on the delay.

18. The ultrasound diagnostic apparatus according to claim 1, further comprising:
a device configured to generate a reception signal of a virtual element which is the shallower point based on a reception time or a reception wave at the shallower point,
wherein the image generating device generates the image from the reception signals of the virtual element, based on the hypothetical sound velocity set in the region including the two or more points.

19. The ultrasound diagnostic apparatus according to claim 1, further comprising:
a point setting device configured to set at least one of the two or more points on a boundary between regions with a uniform sound velocity in the object.

20. The ultrasound diagnostic apparatus according to claim 1, further comprising:
a display device configured to display a calculation result of the local sound velocity.

21. The ultrasound diagnostic apparatus according to claim 20, further comprising:
an amplitude image generation device configured to generate an amplitude image indicating an amplitude of the ultrasonic detection signal with brightness of a dot,
wherein the display device displays the calculation result of the local sound velocity so as to be superimposed on the amplitude image or so as to be displayed in line with the amplitude image.

22. The ultrasound diagnostic apparatus according to claim 20, further comprising:
an amplitude image generation device configured to generate an amplitude image indicating an amplitude of the ultrasonic detection signal with brightness of a dot,
wherein the display device displays the calculation result of the local sound velocity by changing brightness or color of the amplitude image.

23. The ultrasound diagnostic apparatus according to claim 20, further comprising:
a display mode switching device configured to switch a display mode between a first display mode in which only the amplitude image is displayed and a second display mode in which the calculation result of the local sound velocity in the object is displayed.

24. The ultrasonic diagnosis method according to claim 8, further comprising:
performing different transmission focus of the ultrasound waves on each of the two or more points when the received signals are obtained from each of the two or more points.

25. The ultrasound diagnostic method according to claim 8, wherein the generating the image includes obtaining a delay based on a propagation time calculated based on hypothetical sound velocity set in the region including the two or more points and the reception time of the shallower points, and generating the image based on the delay.

26. The ultrasound diagnostic method according to claim 8, further comprising:
generating a reception signal of a virtual element which is the shallower point based on a reception time or a reception wave at the shallower point,
wherein the generating the image generates the image from the reception signals of the virtual element, based on the hypothetical sound velocity set in the region including the two or more points.

27. The ultrasound diagnostic method according to claim 8, further comprising:
setting at least one of the two or more points on a boundary between regions with a uniform sound velocity in the object.

28. The ultrasound diagnostic method according to claim 8, further comprising:
displaying a calculation result of the local sound velocity on a display device.

29. The ultrasound diagnostic method according to claim 28, further comprising:
generating an amplitude image indicating an amplitude of the ultrasonic detection signal with brightness of a dot,
wherein the display device displays the calculation result of the local sound velocity so as to be superimposed on the amplitude image or so as to be displayed in line with the amplitude image.

30. The ultrasound diagnostic method according to claim 28, further comprising:
generating an amplitude image indicating an amplitude of the ultrasonic detection signal with brightness of a dot,
wherein the display device displays the calculation result of the local sound velocity by changing brightness or color of the amplitude image.

31. The ultrasound diagnostic method according to claim 28, further comprising:
switching a display mode between a first display mode in which only the amplitude image is displayed and a second display mode in which the calculation result of the local sound velocity in the object is displayed, by a display mode switching device.

* * * * *